US00PP35075P3

(12) United States Plant Patent
Nishikawa

(10) Patent No.: US PP35,075 P3
(45) Date of Patent: Mar. 28, 2023

(54) ***BIDENS* PLANT NAMED 'ANGEL ROUGE'**

(50) Latin Name: *Bidens laevis*
Varietal Denomination: Angel Rouge

(71) Applicant: Tsunotan IP Co., Ltd., Hagiwara-cho (JP)

(72) Inventor: Koichiro Nishikawa, Naghi-cho (JP)

(73) Assignee: Tsunotan IP Co,. Ltd., Ichinomiya (JP)

( * ) Notice: Subject to any disclaimer, the term of this patent is extended or adjusted under 35 U.S.C. 154(b) by 0 days.

(21) Appl. No.: 15/932,616

(22) Filed: Mar. 23, 2018

(65) Prior Publication Data

US 2018/0279531 P1 Sep. 27, 2018

(30) Foreign Application Priority Data

Mar. 24, 2017 (JP) ..... 31958

(51) Int. Cl.
*A01H 5/02* (2018.01)
*A01H 6/14* (2018.01)

(52) U.S. Cl.
USPC ..... Plt./410
CPC ..... *A01H 6/14* (2018.05)

(58) Field of Classification Search
USPC ..... Plt./410
CPC ..... A01H 5/02
See application file for complete search history.

*Primary Examiner* — Kent L Bell
(74) *Attorney, Agent, or Firm* — The Webb Law Firm

(57) ABSTRACT

A new and distinct *Bidens* plant having dark, orange-red colored ray florets and a compact growth habit.

5 Drawing Sheets

Botanical classification: *Bidens laevis.*
Varietal denomination: 'Angel Rouge'.

CROSS REFERENCE TO RELATED APPLICATION(S)

This application claims the benefit of priority from Japanese Plant Variety Protection Application No. 31958, filed Mar. 24, 2017, which is incorporated herein by reference in its entirety.

BACKGROUND OF THE INVENTION

The present invention comprises a new and distinct *Bidens laevis* plant known by the varietal name 'Angel Rouge'. The new variety is the result of a planned breeding program with the purposes of providing *Bidens* plants with a red flower color and a compact growth habit. The breeding process leading up to 'Angel Rouge' began in 2012 from the applicant's proprietary collection of *Bidens* plants. Ultimately, 'Angel Rouge' is the result of a 2014 cross between *Bidens* L. varieties referred to as BR5-3 (female parent, unpatented) and Nunca Y-1 (male parent, unpatented) and was discovered in 2015 in Aichi Prefecture, Japan. The first asexual reproduction of the new variety was conducted by cuttings in 2016 in Aichi Prefecture, Japan. 'Angel Rouge' has been trial and field tested and has been found to retain its distinctive characteristics and remain true to type through successive asexual propagations. The present invention has not been evaluated under all possible environmental conditions. The phenotype may vary with variations in environment without a change in the genotype of the plant.

When 'Angel Rouge' is compared to *Bidens* L. 'Angel Cheek' (unpatented), both varieties exhibit a compact growth habit and orange-red colored ray florets. However, the ray florets of 'Angel Rouge' have a solid and dark, orange-red colored upper surface, while the ray florets of 'Angel Cheek' have a lighter, primary orange-red color and a secondary orange-yellow color present at the upper surface base and tip. Further, 'Angel Rouge' exhibits no to less anthocyanin stem coloration when compared to 'Angel Cheek', which has weak anthocyanin stem coloration. Additionally, 'Angel Rouge' has an earlier time of flowering than 'Angel Cheek'.

The following traits distinguish 'Angel Rouge' as a new and distinct cultivar from other *Bidens* varieties known to the breeder:

1. Compact growth habit;
2. Short plant height;
3. Absent or very weak anthocyanin stem coloration;
4. Pinnate leaves;
5. Medium-sized leaves;
6. No leaf variegation present;
7. Single inflorescences (less than 8 ray florets);
8. Medium inflorescence diameter;
9. Medium ray floret length and width;
10. Shallow ray floret apex incisions;
11. Solid and dark, orange-red colored upper surface of ray florets;
12. Early time of flowering; and
13. Continuous flowering habit.

DESCRIPTION OF THE DRAWINGS

The accompanying photographic images captured on Mar. 7, 2017 illustrate the new variety, with the colors being as nearly true as is possible with color illustrations of this type.

DESCRIPTION OF THE PLANT

Figure 1:
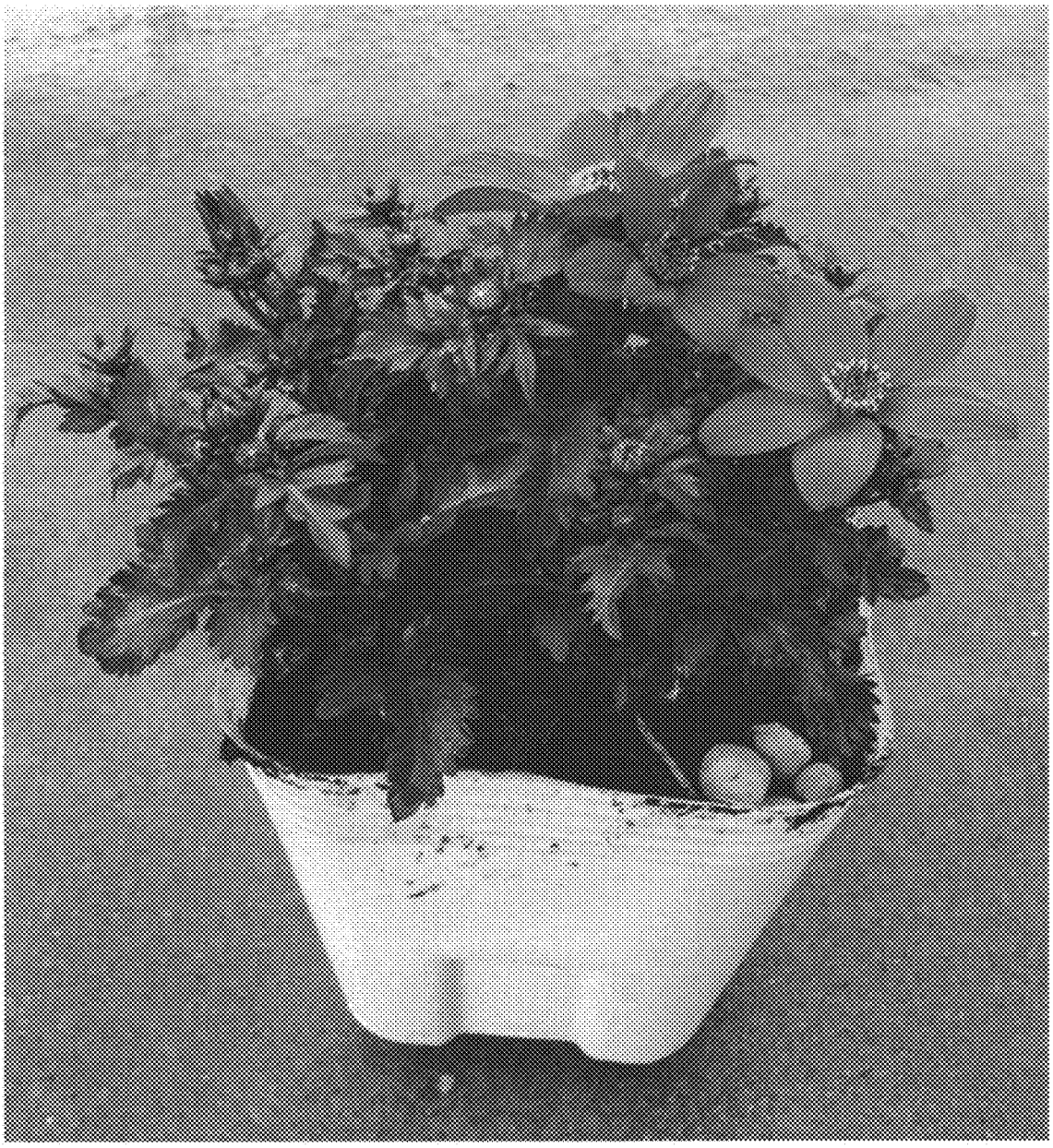
FIG. 1 illustrates an entire flowering plant of the new variety.
Figure 2:
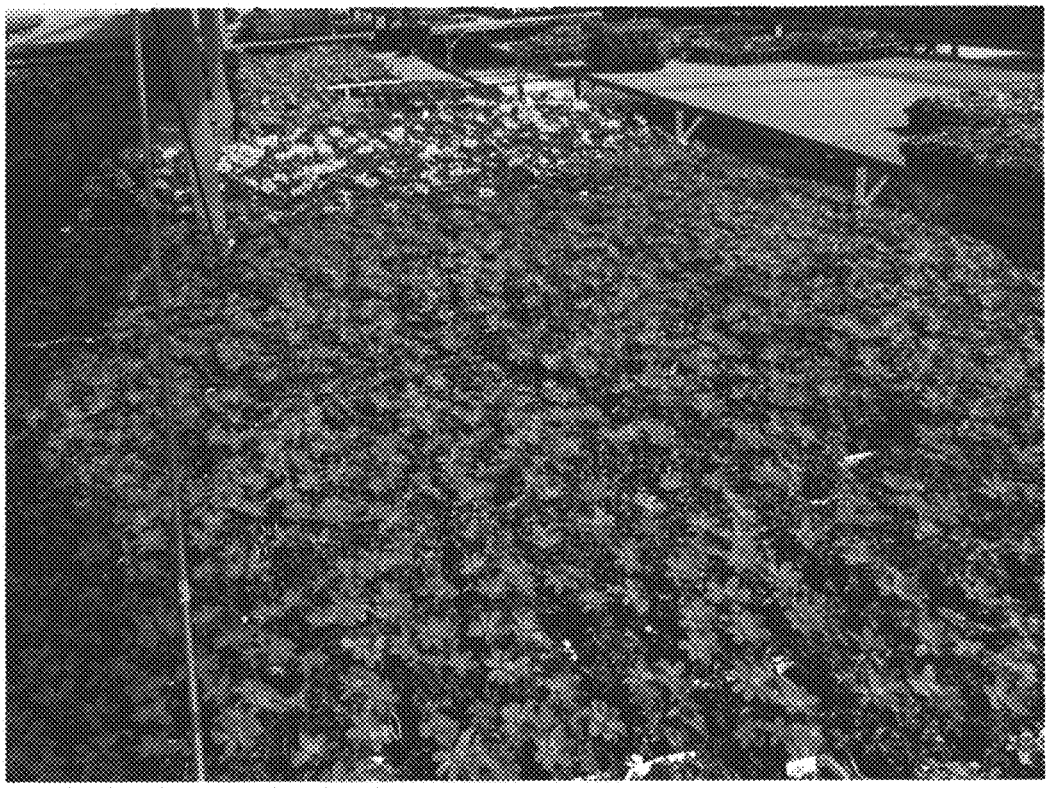
FIG. 2 illustrates numerous flowering plants of the new variety.
Figure 3:
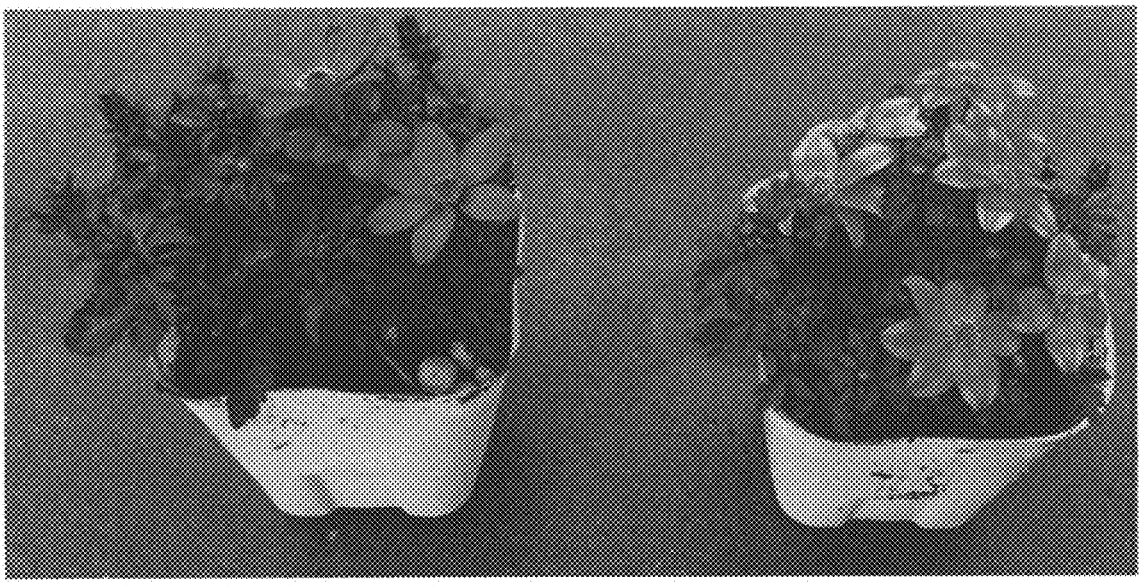
FIG. 3 illustrates a flowering plant of 'Angel Rouge' (left hand side) and its comparison variety, 'Angel Cheek' (right hand side)
Figure 4:
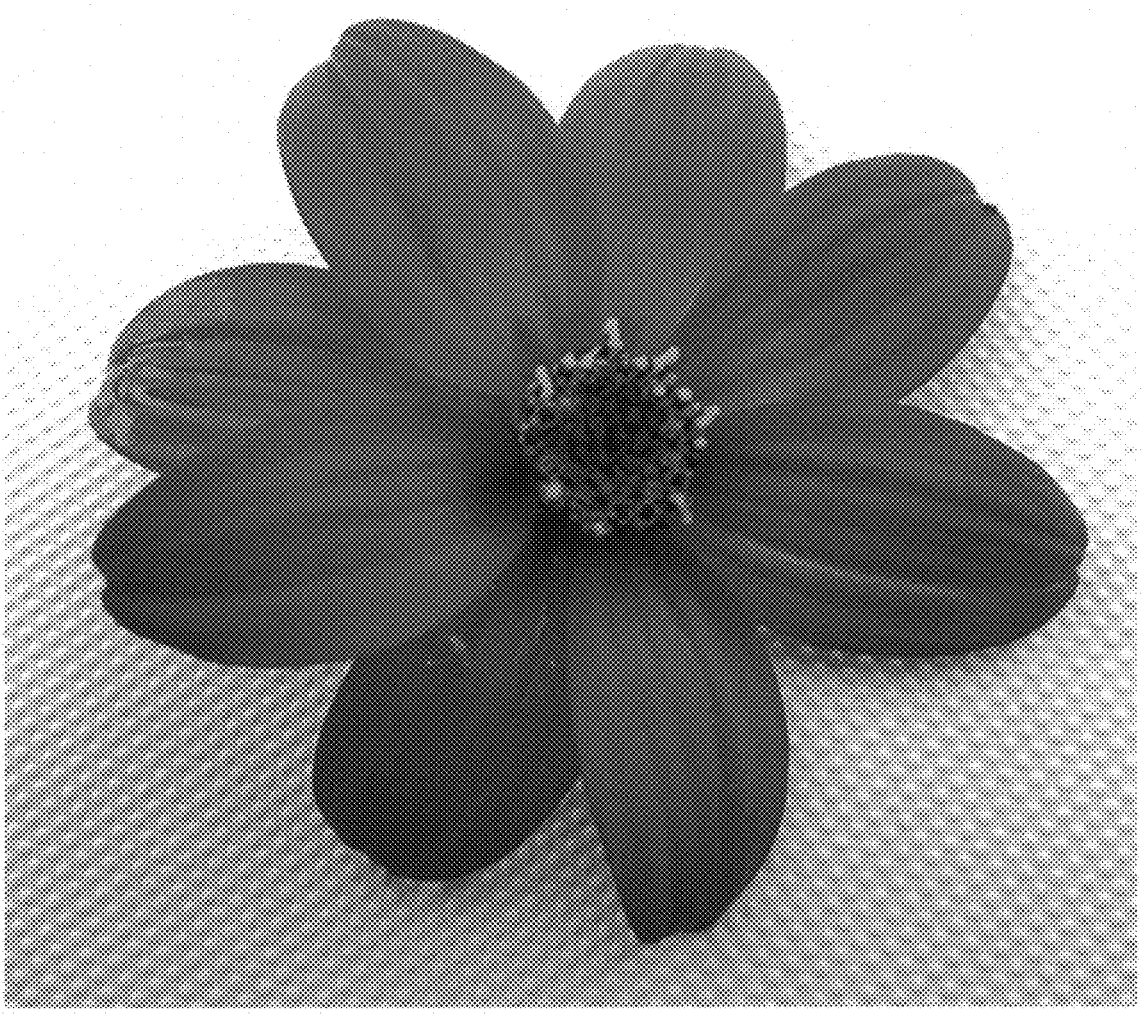
FIG. 4 illustrates the upper surface of an inflorescence of the new variety.
Figure 5:
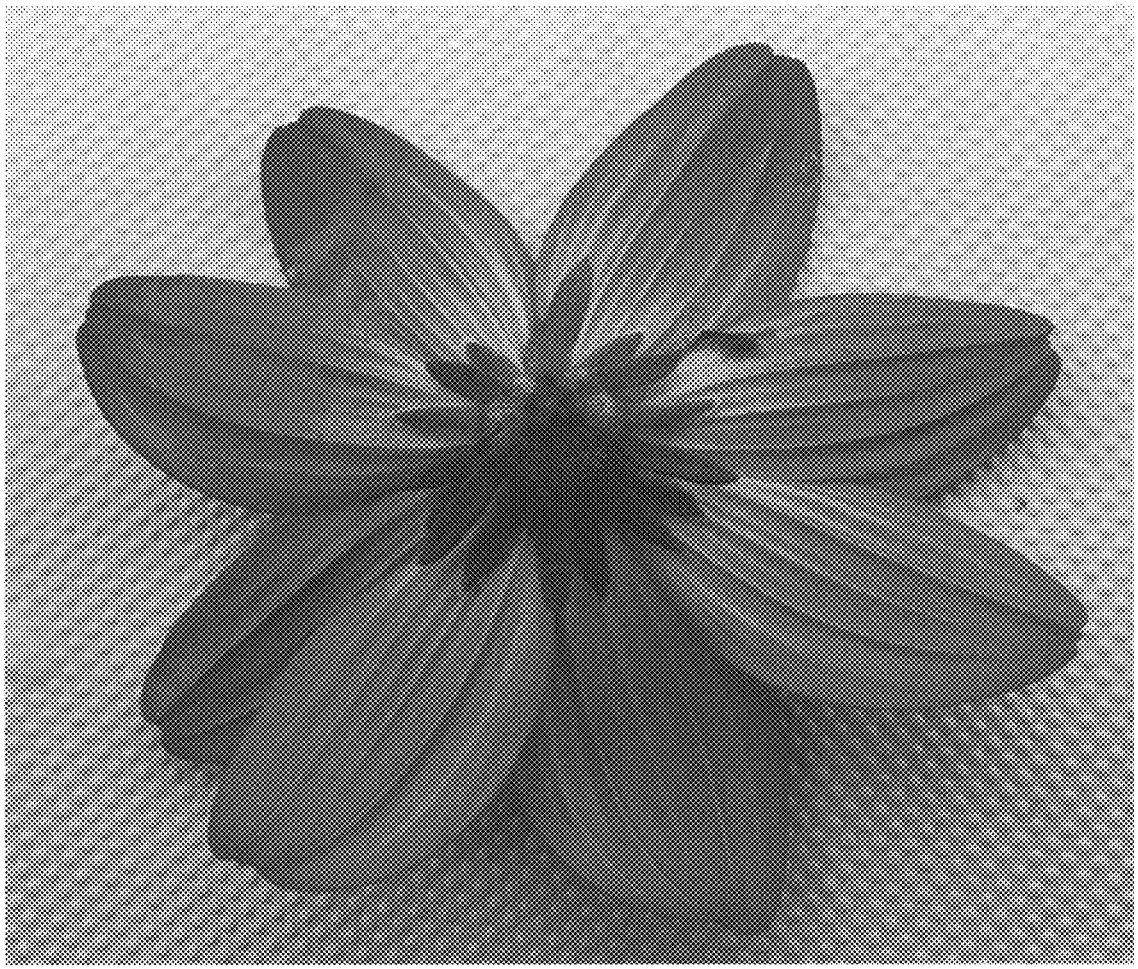
FIG. 5 illustrates the lower surface of an inflorescence of the new variety.

The following detailed description sets forth the characteristics of the new variety. The data which defines these characteristics was collected in Aichi Prefecture, Japan under natural light and the new variety was grown in pots having a diameter of 15 cm. The color determination is in accordance with the JHS/Japan Horticulture Scale Color Chart except where general color terms of ordinary dictionary significance are used.

Plant:

*Intended use*.—For planting and gardening purposes.

*Optimal planting/cutting season*.—From the beginning of December to the beginning of January and from late August to the beginning of November in Aichi Prefecture, Japan.

*Overall plant shape*.—Compact and upright.

*Plant height* (*at one year*).—18.0 cm.

*Plant diameter* (*at one year*).—18.0 cm.

*Stem anthocyanin coloration*.—Absent or very weak; JHS/Japan Horticultural Scale Color Chart 9714 when present.

*Lateral branches*.—Habit: Moderately spreading outward. Number: Numerous. Length: 16.0 cm. Diameter: 1.0 mm. Internode length: 20.0 mm. Texture: Pubescence present. Color: Dark green-yellow (JHS/Japan Horticultural Scale Color Chart 2912).

*Leaves*.—Shape: Trifoliate. Length: 15.0 mm. Width: 13.0 mm. Apex: Generally acute. Base: Acute. Margin: Entire. Size: Medium. Color: Dark green (JHS/Japan Horticultural Scale Color Chart 3508). Variegation: Absent. Texture: Pubescence present on both surfaces. Venation: Prominent main vein present.

*Petiole*.—Length: 6.0 mm. Diameter: 0.9 mm. Color: Pale yellow-green (JHS/Japan Horticultural Scale Color Chart 3303) with edging of dark ruby (JHS Color Chart 0109).

Inflorescence:

*Natural flowering season*.—From late October to late June in Aichi Prefecture, Japan.

*Time of flowering*.—Early.

*Longevity*.—3 days.

*Height*.—7.0 mm.

*Diameter*.—32.0 mm.

*Disc diameter*.—3.0 mm.

*Type and habit*.—Single (less than 8 ray florets) and continuous.

*Inflorescence position*.—Above foliage.

*Number per plant*.—At least 20.

*Fragrance*.—Present.

*Buds*.—Shape: Spherical. Length: 3.0 mm. Diameter: 2.0 mm. Color: Pale yellow-green (JHS/Japan Horticultural Scale Color Chart 3503).

*Receptacle*.—Height: 3.0 mm. Diameter: 3.0 mm. Shape: Almost spherical (aspect ratio of 1). Color: Dark yellow-green (JHS/Japan Horticultural Scale Color Chart 3513).

*Ray florets*.—Length: 16.0 mm. Width: 9.5 mm. Shape: Oval. Apex: Rounded with shallow incisions. Margin: Entire. Number per inflorescence: 8. Texture: Smooth, with numerous indentations along the length. Color: Upper surface: Solid and dark, orange-red (JHS/Japan Horticultural Scale Color Chart 0714). Lower surface: Dark, orange-red (JHS/Japan Horticultural Scale Color Chart 0714) with striations of yellow-orange (JHS Color Chart 2204). Ground color: Solid and dark, orange-red (JHS/Japan Horticultural Scale Color Chart 0714).

*Disc florets*.—Length: 38.0 mm. Diameter: 32.0 mm. Shape: Tubular. Apex: Quilled. Base: See receptacle — rounded. Margins: Entire. Number per inflorescence: Approximately 100. Color: See receptacle — dark yellow-green (JHS/Japan Horticultural Scale Color Chart 3513).

*Phyllaries*.—Number: 6 and rarely duplicative. Shape: Lanceolate. Length: 3.0 mm. Width: 1.0 mm. Apex: Acute. Margin: Entire. Base: See receptacle — dividing into 6 limbs. Color: Both surfaces are reseda (JHS/Japan Horticultural Scale Color Chart 3516).

*Peduncle*.—Length: 27.0 mm. Diameter: 0.8 mm. Texture: Pubescence present on both surfaces. Color: Reseda (JHS/Japan Horticultural Scale Color Chart 3516).

*Reproductive organs*.—Androecium and gynoecium are concentrated in disc florets. Androecium is not produced in ray florets.

I claim:

1. A new and distinct variety of *Bidens* plant named 'Angel Rouge', as is herein illustrated and described.

* * * * *